United States Patent [19]

Leibinsohn

[11] Patent Number: 5,074,289

[45] Date of Patent: Dec. 24, 1991

[54] TRACTION SPLINT

[76] Inventor: Saul Leibinsohn, 24 Lipski Street, 62 195 Tel Aviv, Israel

[21] Appl. No.: 659,667

[22] Filed: Feb. 25, 1991

[30] Foreign Application Priority Data

Mar. 6, 1990 [IL] Israel .......................... 93648

[51] Int. Cl.⁵ .......................... A61F 3/00; A61F 5/04; A61F 5/37
[52] U.S. Cl. .............................. 128/80 R; 128/84 A; 128/87 R; 128/882
[58] Field of Search ................ 128/84 A, 878, 84 C, 128/87 R, 80 R, 877, 879, 85, 882, 80 A, 75, 84 R, 84 B, 87 C; 5/445

[56] References Cited

U.S. PATENT DOCUMENTS

| 2,094,510 | 9/1937 | Watt | 128/84 A |
|---|---|---|---|
| 2,129,635 | 9/1938 | Anderson | 128/84 A |
| 2,454,319 | 11/1948 | Henderson | 128/84 A |
| 4,254,766 | 3/1981 | Kordis | 128/87 R |
| 4,665,905 | 5/1987 | Brown | 128/84 R |
| 4,681,097 | 7/1987 | Pansiera | 128/77 |
| 4,708,131 | 11/1987 | Kendrick | 128/84 R |
| 4,944,290 | 7/1990 | Hepburn | 128/77 |
| 4,964,400 | 10/1990 | Laico | 128/77 |

Primary Examiner—Robert A. Hafer
Assistant Examiner—Michael Brown
Attorney, Agent, or Firm—Benjamin J. Barish

[57] ABSTRACT

A traction splint particularly useful for supporting a fractured leg in traction includes a rigid frame having a pair of longitudinally-extending frame members attachable at the inner end to the fractured leg and connected together at their opposite ends to receive the outer end of the leg. The outer end of the frame includes a pair of attachment jaws formed with a concave configuration for receiving the lower ends of the tibia and fibula and for limiting against the internal and external malleolus; the attachment jaws being carried by the supporting member extending transversely across, and slidable longitudinally of, the pair of frame members at the outer end of the frame.

20 Claims, 2 Drawing Sheets

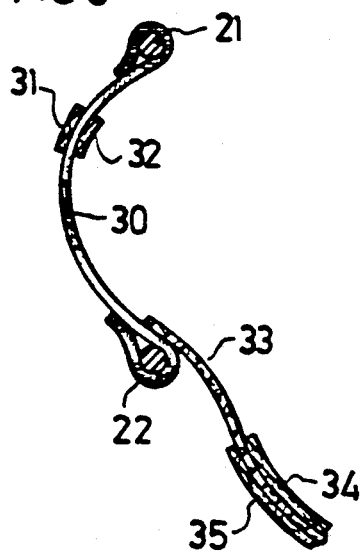
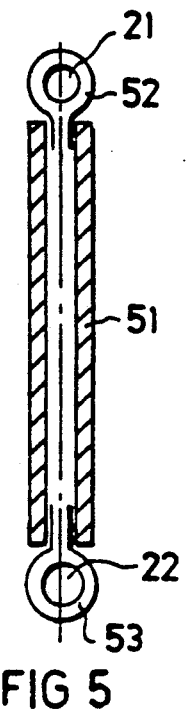
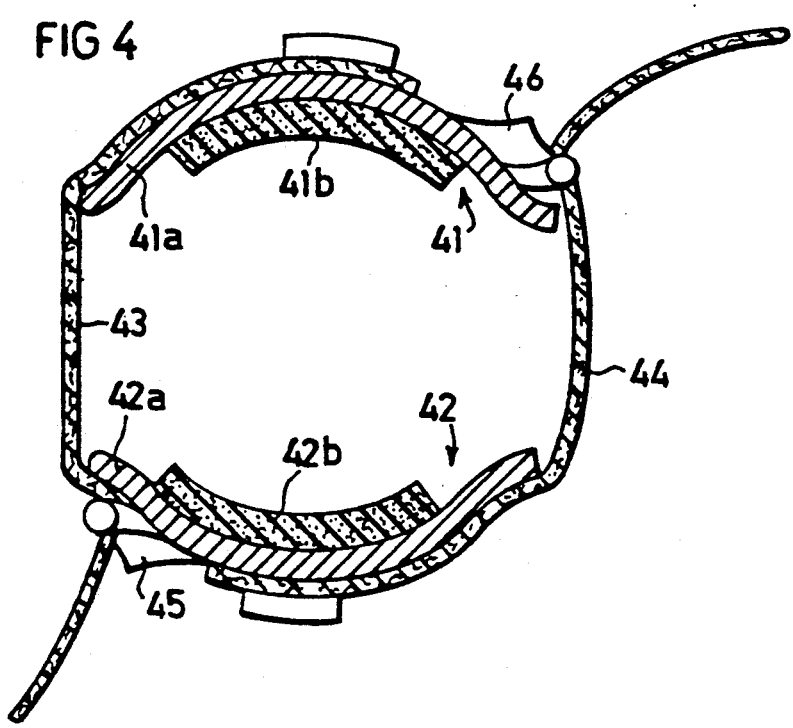

TRACTION SPLINT

FIELD AND BACKGROUND OF THE INVENTION

The present invention relates to a traction splint for supporting a fractured limb in traction. The invention is particularly useful with the Thomas traction splint commonly used for supporting a fractured leg in traction, and is therefore described below with respect to this application, but it will be appreciated that the invention, or certain features thereof, could also be advantageously used in other types of traction splints.

The Thomas traction splint includes a rigid frame having a pair of longitudinally-extending frame members attachable at one end, constituting the inner end of the frame, to the fractured leg to extend on opposite sides thereof, and connected together at the opposite end, constituting the outer end of the frame, to receive the outer end of the leg. The Thomas splint further includes attachment means at the inner end of the frame for attaching it to the leg, and attachment means at the outer end of the frame for attaching the outer end of the leg to it and for applying traction thereto. In the conventional Thomas splint, the latter attachment means generally includes a belt or a sock attachable around the ankle of the leg for applying traction to the leg.

In such a construction, there is danger of interfering with the blood circulation where the belt or sock is attached to the leg. In addition, if there is damage to the calcaneous tendon, such a construction can increase the damage. Further, in such a construction, particularly where a sock is used, the sock cover a relatively large surface area of the foot which, if injured, increases the difficulty for treatment.

OBJECTS AND BRIEF SUMMARY OF THE INVENTION

An object of the present invention is to provide a traction splint of the foregoing type but having a number of advantages over the known construction.

According to the present invention, there is provided a traction splint particularly useful for supporting a fractured leg in traction, comprising: a rigid frame having a pair of longitudinally-extending frame members attachable at one end, constituting the inner end, to the fractured leg to extend on opposite sides thereof and connected together at their opposite ends, constituting the outer end of the frame, by an interconnection to receive the outer end of the leg; attachment means at the inner end of the frame for attaching it to the leg; and attachment means at the outer end of the frame for attaching it to the outer end of the leg. The attachment means at the outer end of the frame comprises a pair of attachment jaws formed with a concave configuration for receiving the lower ends of the tibia and fibula and for limiting against the internal and external malleolus. The splint further includes traction means applied between the interconnection at the outer end of the frame and the pair of attachment jaws for applying traction to the pair of attachment jaws and thereby to the ends of the tibia and fibula.

According to further features in the described preferred embodiment, each of the attachment jaws includes a rigid plate of concave configuration lined on its inner face with a cushioning material. In addition, the attachment jaws further include a pair of transversely-extending belts each having one end attached to one attachment jaw, with the opposite end attachable to a buckle carried by the other attachment jaw.

According to further features in the described preferred embodiment, the attachment jaws are carried by a supporting member extending transversely across, and slidable longitudinally of, the pair of frame members at the outer end of the frame. More particularly, the attachment jaws are carried at one of the ends of a further pair of belts, the opposite ends of the further pair of belts being attachable to further buckles carried by the supporting member. The traction splint includes a still further belt attached at one end to the outer end of the frame and attachable at its opposite end to a still further buckle carried by the supporting member for applying traction to the leg.

A traction splint constructed in accordance with the foregoing features secures the lower end of the foot with less danger of interfering with blood circulation, and with less danger of increasing the damage to the calcaneous tendon if damaged. In addition, the arrangement exposes more surface area of the foot for treatment if necessary.

According to a further aspect of the present invention, there is provided a traction splint of the type described above, characterized in that the attachment means at the inner end of the frame comprises: a web of flexible sheet material attached at its opposite edges to the inner ends of the pair of frame members and extending for a part of the length of the frame members; the web having a width larger than the space between the frame members so as to enable it to be flipped to either side for attachment to a left leg or a right leg; a fastening strip carried on each face of the web and extending longitudinally thereof; and at least one strap attached at one end to the web and carrying a fastening strip on each of its two faces on its opposite end.

Further features and advantages of the invention will be apparent from the description below.

BRIEF DESCRIPTION OF THE DRAWINGS

The invention is herein described, by way of example only, with reference to the accompanying drawings, wherein:

FIG. 3 is a sectional view along line III—III of FIG. 1;

FIG. 4 is a sectional view along line IV—IV of FIG. 2; and

FIG. 5 is a sectional view along line V—V of FIG. 2.

DESCRIPTION OF A PREFERRED EMBODIMENT

Figure 1:
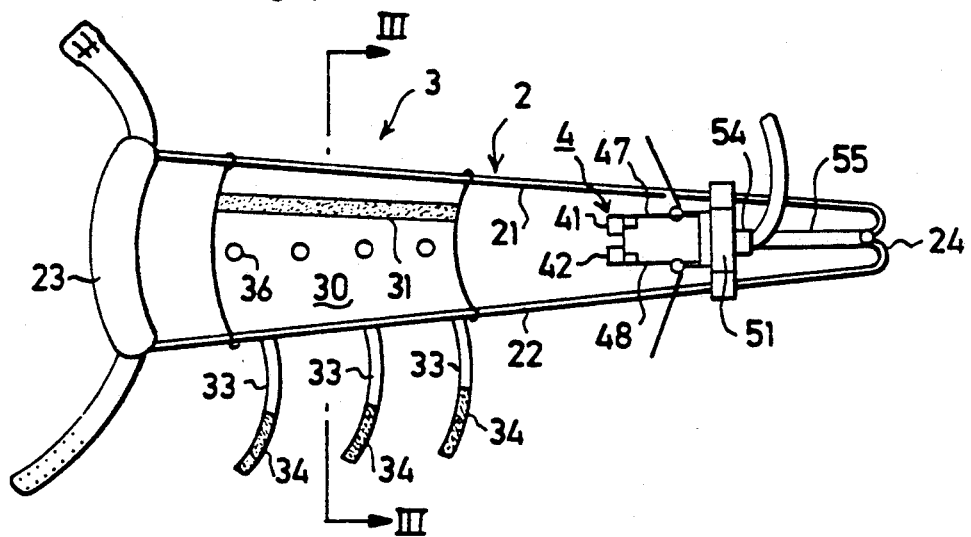
FIG. 1 illustrates one form of traction splint constructed in accordance with the present invention.

The traction splint illustrated in the drawings is of the Thomas type particularly useful for supporting a fractured leg in traction. It comprises a rigid frame, generally designated 2; attachment means, generally designated 3, at one end of the frame (constituting the inner end) for attachment to the leg; and further attachment means, generally designated 4, at the opposite end of the frame (constituting the outer end) for attachment to the outer end of the leg and for applying traction thereto.

More particularly, the rigid frame 2 comprises a longitudinally-extending frame member 21 and a slightly longer frame member 22 connected together at their inner ends by a curved pad 23 and at their outer ends by a connecting member 24. Preferably, the rigid frame 2 is made of a single metal or plastic rod of circular cross-section bent into the U-configuration illustrated in FIG. 1 to form the two longitudinally-extending frame members 21, 22 interconnected at one end by frame member 24, and the curved pad 23 is then applied to interconnect the other ends of the frame members and to facilitate attaching it to the upper end of the leg by the attachment means 3. The connecting member 24 is formed with an outwardly-opening bend cooperable with the attachment means 4 attachable to the outer end of the leg for applying traction to the leg when the frame is attached thereto.

The inner attachment means 3 for attaching the frame to the inner end of the leg comprises a web 30 of flexible sheet material, such as fabric or plastic, attached at its opposite edges to the inner ends of the two frame members 21, 22. Fabric web 30 is of a width larger than the space between the two frame members thereby enabling the web to be flipped to either side, for attachment to the right leg or to the left leg, as the case may be. Web 30 is of a length approximately one-half the length of the complete frame so as to be attachable to the upper portion of the leg above the knee.

An attachment strip 31, such as of a "Velcro" (Reg. TM) hook-and-loop plastic fastener strip, is fixed to one face of web 30 and extends for its complete length; and a similar attachment strip 32 is fixed to the opposite face of the web and also extends for its complete length in registration with attachment strip 31. It will thus be seen that when web 30 is flipped to one side (the side illustrated in FIG. 3), Velcro strip 31 is exposed on the outer face of the web; and when the web is flipped to the opposite side, Velcro strip 32 is exposed on its outer face.

Attachment means 3 at the inner end of the frame further includes a plurality of straps 33 attached at one end to frame member 22. The opposite ends of the straps 33 carry further Velcro strips 34, 35 on its opposite faces cooperable with Velcro strips 31, 32 carried by the web 30. Thus, each of the belts may be applied with either of its Velcro strips 34, 35 engaging the outwardly-facing Velcro strip 31, 32 in order to fix the inner end of the frame to the fractured leg.

As shown in FIG. 1, web 30 is formed with a plurality of openings 36, which serve as drainage openings for draining the leg when the frame is attached thereto.

Figure 2:
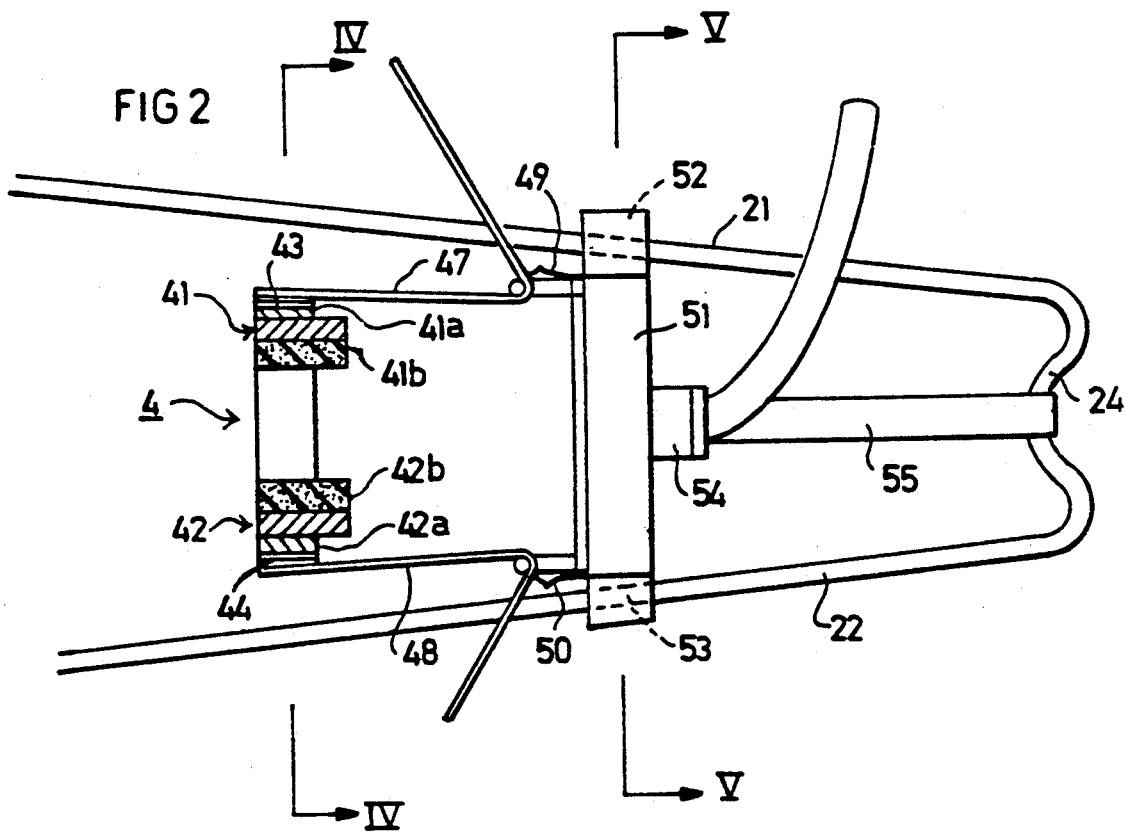
FIG. 2 is a enlarged fragmentary view illustrating the lower end of the traction splint of FIG. 1.

The outer attachment means 4, used for attaching the outer end of the fractured leg to the frame and for applying traction to the leg, is best seen in FIG. 2. It comprises a pair of attachment members or jaws 41, 42 formed with a concave configuration for receiving the lower ends of the tibia and fibula and for limiting against the internal and external malleolus. Each of the attachment jaws 41, 42 includes a rigid plate 41a, 42a, e.g., of metal, of concave configuration lined on its inner face with a cushioning material 41b, 42b, such as rubber or sponge rubber. Attachment means 4 further includes a pair of belts 43, 44 each attached at one end to one of the rigid plates 41a, 42a of the attachment jaw, with the opposite end of each belt passing through a buckle 45, 46 attached to the rigid plate of the other jaw. Thus, belt 43 attached to jaw 41 passes through a buckle 45 carried by jaw 42; and similarly, belt 44 attached to jaw 42 passes through a buckle 46 carried by jaw 41. The two buckles 45, 46 are of the self-locking type, which permit their respective belts to be drawn in one direction through the buckle for tightening the belt onto the subject's leg, but self-lock as soon as the belt is released.

The two attachment jaws 41, 42 include a second pair of belts 47, 48 also attachable at one end to the rigid plate 41a, 42a, of the respective jaw. Belts 47, 48, however, extend in the axial direction, and their opposite ends are receivable in buckles 49, 50 carried by a supporting member 51 extending transversely across the two frame members 21, 22.

Supporting member 51, of rigid material such as metal, is formed at its opposite ends with a pair of openings or eyes 52, 53 slidably receiving the two frame members 21, 22 to permit the supporting member 51 to be slid along the length of the frame members. Its inner face carries the two buckles 49, 50, receiving the belts 47, 48, and its outer face carries a further buckle 54 receiving one end of a further belt 55 whose opposite end is fixed to the connecting frame member 24 at its U-shaped bend.

The manner of applying the traction splint illustrated in the drawings will be apparent from the above description. Thus, the inner attachment assembly 3 is applied to the inner end of the fractured leg by flipping the belt 43 to either side depending on whether the leg is a left leg or a right leg. The straps 33 may then be applied across the side of the leg opposite to that engaged by the web 30 for securing the traction splint to the upper end of the injured leg. Since both faces of the web 30 carry the Velcro strips 31, 32, and since the Velcro strips extend longitudinally of the splint, it will be seen that the belts 33, which also carry the Velcro strips 34, 35 on both faces, may be applied transversely or diagonally of the leg, according to the particular condition of the leg.

After the traction splint has thus been attached to the inner end of the fractured leg, the two attachment jaws 41, 42 are then placed against the lower ends of the tibia and fibula bones limiting against the internal and external malleolus. The two straps 43, 44 are then tightened by means of the self-locking buckles 45, 46 to secure the two jaws to the leg. The two belts 47, 48 are then tightened to the supporting member 51 by means of the self-locking buckles 49, 50. Finally belt 55 is tightened by means of the self-locking buckle 54, to apply traction to the supporting member 51, and thereby to the fractured leg engaged by the jaws 41, 42.

Since the jaws 41, 42 engage the sides of the leg adjacent to and abutting against the internal and external malleolus, they do not interfere with the blood vessels at the front and rear sides of the leg, nor with the calcaneous tendon at the rear side of the leg.

While the invention has been described with respect to a preferred embodiment, it will be appreciated that many variations may be made. For example, other forms of attachment strips, such as drawstrings, buttons, or the like, could be used instead of the Velcro strips. In addition, the traction splint, or various features thereof, particularly the inner attaching device, could be used in other types of traction splints particularly of the disassemble types. Many other variations, modifications and application of the invention will be apparent.

What is claimed is:

1. A traction splint particularly useful for supporting a fractured leg in traction, comprising:
   a rigid frame having a pair of longitudinally-extending frame members attachable at one end, constituting the inner end, to the fractured leg to extend on opposite sides thereof and connected together at their opposite ends, constituting the outer end of the frame, by an interconnection to receive the outer end of the leg;

attachment means at the inner end of the frame for attaching it to the leg;

attachment means at the outer end of the frame for attaching it to the outer end of the leg;

said attachment means at the outer end of the frame comprising a pair of attachment jaws formed with a concave configuration for receiving the lower ends of the tibia and fibula and for limiting against the internal and external malleolus;

and traction means applied between said interconnection at said outer end of the frame and said pair of attachment jaws for applying traction to said pair of attachment jaws and thereby to the ends of the tibia and fibula.

2. The traction splint according to claim 1, wherein each of said attachment jaws includes a rigid plate of concave configuration lined on its inner face with a cushioning material.

3. The traction splint according to claim 2, wherein said attachment jaws further include a pair of transversely-extending belts each having one end attached to one attachment jaw, with the opposite end attachable to a buckle carried by the other attachment jaw.

4. The traction splint according to claim 1, wherein said attachment jaws are carried by a supporting member extending transversely across, and slidable longitudinally of, said pair of frame members at the outer end of the frame.

5. The traction splint according to claim 4, wherein said attachment jaws are carried at one of the ends of a pair of belts, the opposite ends of said pair of belts being attachable to buckles carried by said supporting member.

6. The traction splint according to claim 4, wherein the rigid frame includes a further belt attached at one end to the outer end of the frame and attachable at its opposite end to a further buckle carried by said supporting member for applying traction to the leg.

7. The traction splint according to claim 1, wherein said attachment means at the inner end of the frame comprises:

a web of flexible sheet material attached at its opposite edges to the inner ends of the pair of frame members and extending for a part of the length of the frame members;

said web having a width larger than the space between said frame members so as to enable it to be flipped to either side for attachment to a left leg or a right leg;

a fastening strip carried on each face of the web and extending longitudinally thereof;

and at least one strap attached at one end to said web and carrying a fastening strip on each of its two faces on its opposite end.

8. The traction splint according to claim 7, wherein the splint includes a plurality of said belts attached to and spaced longitudinally of one of said frame members.

9. The traction splint according to claim 7, wherein said fastening strips carried on each face of the web and of the at least one strap are hook-and-loop plastic fastener strips.

10. The traction splint according to claim 7, wherein said web is formed with a plurality of openings therethrough for drainage purposes.

11. A traction splint particularly useful for supporting a fractured leg in traction, comprising:

a rigid frame having a pair of longitudinally-extending frame members attachable at one end, constituting the inner end, to the fractured leg to extend on opposite sides thereof and connected together at their opposite ends, constituting the outer end of the frame, by an interconnection to receive the outer end of the leg;

attachment means at the inner end of the frame for attaching it to the leg;

attachment means at the outer end of the frame for attaching it to the outer end of the leg;

said attachment means at the outer end of the frame comprising a pair of attachment jaws formed with a concave configuration for receiving the lower ends of the tibia and fibula and for limiting against the internal and external malleolus;

said attachment jaws being carried by a supporting member extending transversely across, and slidable longitudinally of, said pair of frame members at the outer end of the frame;

and traction means applied between said interconnection at said outer end of the frame and said supporting member for applying traction to said pair of attachment jaws and thereby to the ends of the tibia and fibula.

12. The traction splint according to claim 11, wherein each of said attachment jaws includes a rigid plate of concave configuration lined on its inner face with a cushioning material.

13. The traction splint according to claim 12, wherein said attachment jaws further include a pair of transversely-extending belts each having one end attached to one attachment jaw, with the opposite end attachable to a buckle carried by the other attachment jaw.

14. The traction splint according to claim 11, wherein said attachment jaws are carried at one of the ends of a pair of belts, the opposite ends of said pair of belts being attachable to buckles carried by said supporting member.

15. The traction splint according to claim 11, wherein the rigid frame includes a belt attached at one end to the outer end of the frame and attachable at its opposite end to a buckle carried by said supporting member for applying traction to the leg.

16. The traction splint according to claim 11, wherein said attachment means at the inner end of the frame comprises:

a web of flexible sheet material attached at its opposite edges to the inner ends of the pair of frame members and extending for a part of the length of the frame members;

said web having a width larger than the space between said frame members so as to enable it to be flipped to either side for attachment to a left leg or a right leg;

a fastening strip carried on each face of the web and extending longitudinally thereof;

and at least one strap attached at one end to said web and carrying a fastening strip on each of its two faces on its opposite end.

17. A traction splint particularly useful for supporting a fractured leg in traction, comprising:

a rigid frame having a pair of longitudinally-extending frame members attachable at one end, constituting the inner end, to the leg to extend on opposite sides thereof and connected together at their opposite ends, constituting the outer end of the frame, to receive the outer end of the leg;

attachment means at the inner end of the frame for attaching it to the leg;

and attachment means at the outer end of the frame for attaching it to the outer end of the leg and for applying traction thereto;

characterized in that said attachment means, at the inner end of the frame comprises:

a web of flexible sheet material attached at its opposite edges to the inner ends of the pair of frame members and extending for a part of the length of the frame members;

said web having a width larger than the space between said frame members so as to enable it to be flipped to either side for attachment to a left leg or a right leg;

a fastening strip carried on each face of the web and extending longitudinally thereof;

and at least one strap attached at one end to said web and carrying a fastening strip on each of its two faces on its opposite end.

18. The traction splint according to claim 17, wherein the splint includes a plurality of said belts attached to and spaced longitudinally of one of said frame members.

19. The traction splint according to claim 17, wherein said fastening strips carried on each face of the web and of the at least one strap are hook-and-loop plastic fastener strips.

20. The traction splint according to claim 17, wherein said web is formed with a plurality of openings therethrough for drainage purposes.

* * * * *